US012616699B2

(12) United States Patent
Eliott et al.

(10) Patent No.: US 12,616,699 B2
(45) Date of Patent: *May 5, 2026

(54) OPHTHALMIC FORMULATIONS OF METHOTREXATE

(71) Applicant: Aldeyra Therapeutics, Inc., Lexington, MA (US)

(72) Inventors: Dean Eliott, Carlsbad, CA (US); Stephen Gitu Machatha, Wilmington, MA (US); Pramod Sarpotdar, Roseville, CA (US); Tomasz Stryjewski, Somerville, MA (US)

(73) Assignee: Aldeyra Therapeutics, Inc., Lexington, MA (US)

( * ) Notice: Subject to any disclaimer, the term of this patent is extended or adjusted under 35 U.S.C. 154(b) by 621 days.

This patent is subject to a terminal disclaimer.

(21) Appl. No.: 17/753,721

(22) PCT Filed: Sep. 11, 2020

(86) PCT No.: PCT/US2020/050565
§ 371 (c)(1),
(2) Date: Mar. 11, 2022

(87) PCT Pub. No.: WO2021/051003
PCT Pub. Date: Mar. 18, 2021

(65) Prior Publication Data
US 2022/0370460 A1     Nov. 24, 2022

Related U.S. Application Data

(60) Provisional application No. 63/044,288, filed on Jun. 25, 2020, provisional application No. 62/900,060, filed on Sep. 13, 2019.

(51) Int. Cl.
| | |
|---|---|
| *A61K 31/519* | (2006.01) |
| *A61K 9/00* | (2006.01) |
| *A61K 47/02* | (2006.01) |
| *A61K 47/26* | (2006.01) |

(52) U.S. Cl.
CPC .......... *A61K 31/519* (2013.01); *A61K 9/0048* (2013.01); *A61K 47/02* (2013.01); *A61K 47/26* (2013.01)

(58) Field of Classification Search
None
See application file for complete search history.

(56) References Cited

U.S. PATENT DOCUMENTS

| | | | |
|---|---|---|---|
| 7,166,570 B2 | 1/2007 | Hunter et al. | |
| 9,259,427 B2 | 2/2016 | Tierney et al. | |
| 10,098,884 B2 | 10/2018 | Eliott et al. | |
| 2004/0253243 A1 | 12/2004 | Epstein et al. | |
| 2005/0101605 A1 | 5/2005 | Ahmed et al. | |
| 2005/0255144 A1 | 11/2005 | Schultz | |
| 2006/0073182 A1 | 4/2006 | Wong et al. | |
| 2006/0258698 A1 | 11/2006 | Mudumba et al. | |
| 2008/0241221 A1 | 10/2008 | Whitcup et al. | |
| 2009/0081277 A1 | 3/2009 | Robinson et al. | |
| 2010/0087474 A1 | 4/2010 | Kaushal et al. | |
| 2010/0226992 A1* | 9/2010 | Kabra | A61P 43/00 |
| | | | 977/773 |
| 2011/0200662 A1 | 8/2011 | Glazier | |
| 2014/0105956 A1 | 4/2014 | Banerjee et al. | |
| 2019/0054023 A1 | 2/2019 | Seaman et al. | |
| 2021/0283135 A1 | 9/2021 | Eliott et al. | |
| 2023/0017743 A1 | 1/2023 | Eliott et al. | |
| 2023/0018197 A1 | 1/2023 | Eliott et al. | |
| 2024/0197740 A1 | 6/2024 | Machatha et al. | |

FOREIGN PATENT DOCUMENTS

| | | |
|---|---|---|
| WO | 2006122249 A2 | 11/2006 |
| WO | 2010101971 A1 | 9/2010 |
| WO | 2014033184 A1 | 3/2014 |
| WO | 2014074823 A1 | 5/2014 |
| WO | 2016019165 A1 | 2/2016 |
| WO | 2016067024 A1 | 5/2016 |
| WO | 2017103218 A1 | 6/2017 |
| WO | 2018201146 A1 | 11/2018 |
| WO | 2019169306 A1 | 9/2019 |
| WO | 2021051003 A1 | 3/2021 |
| WO | 2021173929 A1 | 9/2021 |
| WO | 2024129979 A1 | 6/2024 |

OTHER PUBLICATIONS

U.S. Appl. No. 18/081,546, filed Dec. 14, 2022, 102 pages.
Benner et al., "Intravitreal Methotrexate for the Treatment of Proliferative Vitreoretinopathy," BMJ Open Ophthalmol. 2019;4(1).
Gonzalez-Tello et al., "Density and Viscosity of Concentrated Aqueous Solutions of Polyethylene Glycol," J Chem Eng Data. 1994; 39:611-614.

(Continued)

*Primary Examiner* — Genevieve S Alley
(74) *Attorney, Agent, or Firm* — Wolf, Greenfield & Sacks, P.C.

(57) ABSTRACT

The present disclosure provides formulations of methotrexate for ocular administration, including intravitreal administration, and use of the formulations for treating proliferative vitreoretinopathy (PVR), intraocular lymphoma (e.g., PVRL), and intraocular inflammation.

18 Claims, 1 Drawing Sheet

(56)         References Cited

OTHER PUBLICATIONS

Kwon et al., "Retinal Detachment and Proliferative Vitreoretinopathy," Dev Ophthalmol. 2016;55:154-62.

Liu et al., "Pharmacological Clearance of Misfolded Rhodopsin for the Treatment of RHO-Associated Retinitis Pigmentosa," FASEB J. 2020;34(8):10146-10167.

Owen et al., "Preliminary Results Of Treatment With Intravitreal Methotrexate In Patients With Macula Oedema Secondary To Uveitis," ARVO Annual Meeting Abstract; Investigative Ophthalmology & Visual Science. 2012; 53(14):1179.

Regupathi et al., "Densities and Viscosities of Poly(ethylene glycol) 4000 + Diammonium Phosphate Water Systems," J. Chem. Eng. Data. 2009; 54(3):1100-1106.

Sadaka et al., "Intravitreal Methotrexate Infusion for Proliferative Vitreoretinopathy," Clin Ophthalmol. 2016;10:1811-1817.

Sarfare et al., "Biocompatibility of a Synthetic Biopolymer for the Treatment of Rhegmatogenous Retinal Detachment," J Clin Exp Ophthalmol. 2015; 6(5):475.

Schwartz et al., "Tamponade in surgery for retinal detachment associated with proliferative vitreoretinopathy," Cochrane Database Syst Rev. 2014; 2(2):CD006126.

Tween 20 Datasheet; Sigma-Aldrich; Retrieved from the Internet Nov. 19, 2020. 3 pages. https://www.sigmaaldrich.com/catalog/product/roche/11332465001?lang=en&region=US#:~:text=Tween%2020%>.

Yeh and Wilson, "Combination intravitreal rituximab and methotrexate for massive subretinal lymphoma," Eye (Lond). 2010;24(10):1625-7.

PCT International Search Report and Written Opinion from PCT/US2020/050565 dated Dec. 22, 2020.

Alabi, Rolake, MD, Ph.D. et al., "Rescue Intravitreal Methotrexate Treatment Following Early Recognition of Proliferative Vitreoretinopathy," Retinal Cases and Brief Reports, DOI: 10.1097/ICB.0000000000001252, Ophthalmic Communications Society, Inc., Jan. 22, 2022 (13 Pages).

Banerjee, Philip J., et al., "Slow-Release Dexamethasone in Proliferative Vitreoretinopathy," Ophthalmology, vol. 124, No. 6, Jun. 2017, pp. 757-767.

Ma, Wei-Li et al., "Clinical Outcomes of Primary Intraocular Lymphoma Patients Treated With Front-Line Systemic High-Dose Methotrexate and Intravitreal Methotrexate Injection," Ann Hematol, 2016, DOI 10.1007/s00277-015-2582-x, vol. 95, pp. 593-601.

Roca, Jose A. et al., "Adjunctive Serial Post-Operative Intravitreal Methotrexate Injections in the Management of Advanced Proliferative Vitreoretinopathy," Retinal Disorders, Graefe's Archive for Clinical and Experimental Ophthalmology, DOI 10.1007/s00417-021-05206-z, Springer Nature 2021 (5 Pages).

Schiff, William M. et al., "Safety and Efficacy Assessment of Chimeric Ribozyme to Proliferating Cell Nuclear Antigen to Prevent Recurrence of Proliferative Vitreoretinopathy," Arch Ophthalmol, vol. 125, No. 9, Sep. 2007, pp. 1161-1167.

Wa, Christianne April et al., "Post-Operative Intravitreal Methotrexate Injections After Recurrent Retinal Detachment Repair Can Reduce the Risk and Progress of Proliferative Vitreoretinopathy," Investigative Ophthalmology & Visual Science, Jun. 2020, vol. 61, No. 1413 (2 Pages).

Hardwig et al., "The Safety of Intraocular Methotrexate in Silicone-Filled Eyes," Retina, Lippincott, Williams & Wilkins, Aug. 31, 2008, vol. 28, No. 8, pp. 1082-1086.

Idrees et al., "Proliferative Vitreoretinopathy: a Review," International Opthalmogy Clinics, Jan. 1, 2019, pp. 221-240.

Hsu et al., "Clinical outcomes of intravitreal methotrexate injection protocol with a reduced initial frequency for intraocular lymphoma", Journal of the Formosan Medical Association, 2022, 121(1 Pt 2):416-424.

Zhou et al., "Reduced frequency of Intravitreal methotrexate injection lowers the risk of Keratopathy in Vitreoretinal lymphoma patients", BMC Ophthalmology, 2020, 20(1):189, pp. 1-9.

International Search Report and Written Opinion received for PCT Application No. PCT/US2023/084041, dated Mar. 26, 2024, 18 pages.

European Office Action, mailed Feb. 25, 2026, for European Application No. 20863798.3.

* cited by examiner

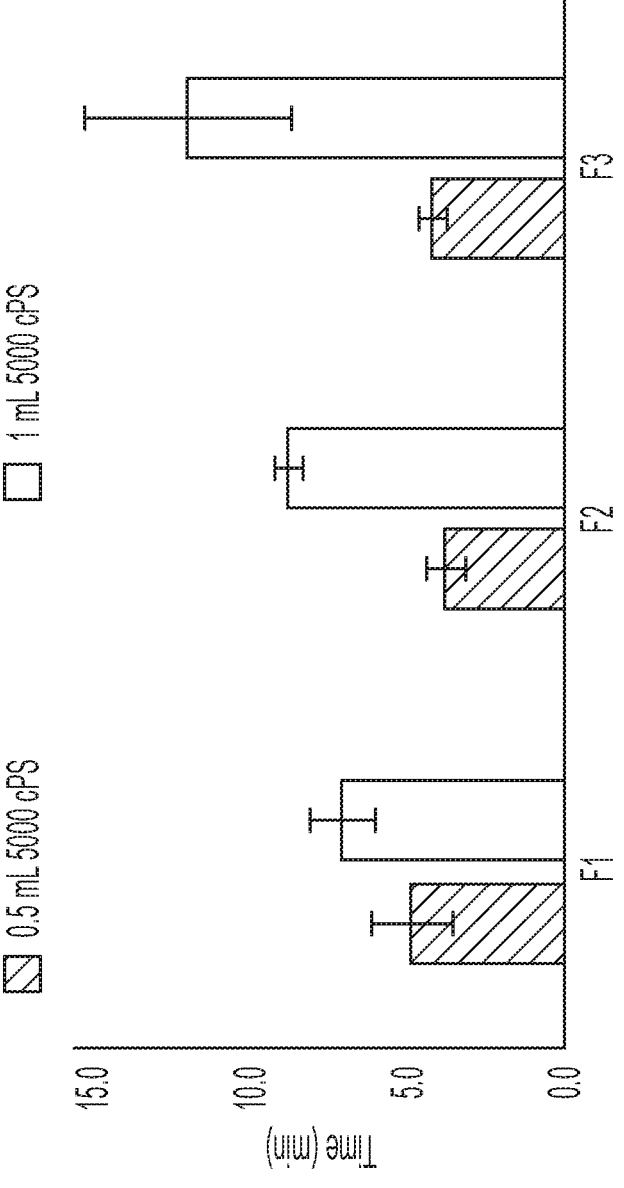

OPHTHALMIC FORMULATIONS OF METHOTREXATE

1. CROSS-REFERENCE TO RELATED APPLICATIONS

This application is a National Stage of International Application No. PCT/US2020/050565, filed Sep. 11, 2020, which claims the benefit under 35 U.S.C. § 119(e) of U.S. Provisional Application No. 63/044,288, filed Jun. 25, 2020, and U.S. Provisional Application No. 62/900,060, filed Sep. 13, 2019; the contents of each of which are incorporated herein by reference in their entirety.

2. BACKGROUND

Proliferative vitreoretinopathy (PVR) is a clinical syndrome that occurs after rhegmatogenous retinal detachment, such as caused by a break in the retina (e.g., retinal tear or retinal hole) and its surgical repair. The pathogenesis of PVR involves the release of cells into the vitreous cavity (extraretinal cells) where they replicate and form periretinal fibrocellular membranes on the inner and/or outer surfaces of the retina, creating shortening of the retina and retinal traction. PVR is characterized by intraretinal fibrosis and reduced elasticity, which leads to tractional elevation of the retina and subsequently new retina breaks and recurrent retinal detachment. PVR can occur in untreated eyes with retinal detachment or after retinal procedures such as retinal cryopexy, laser retinopexy, pneumatic retinopexy, scleral buckle and/or pars plana vitrectomy. The prevalence of PVR varies widely but is estimated to range about 5 to 12% of all rhegmatogenous retinal detachment cases (Kwon et al., Dev Ophthalmol., 2016; 55:154-62). PVR and its associated retinal traction is one of the main reasons for failure (i.e., recurrent retinal detachment) of initially successful repairs of retinal detachment and is present in approximately 75% of failed retinal detachment repairs (Sadaka et al., Clinical Ophthalmology, 2016; 10 1811-1817).

Retinal detachment surgery can include scleral buckling, pneumatic retinopexy, and pars plana vitrectomy (PPV). Pneumatic retinopexy involves injecting gas into the vitreous cavity while PPV for retinal detachment involves removal of the vitreous and its replacement with a tamponade agent, such as silicone oil or gas. Tamponade agents provide surface tension across retinal breaks, preventing further fluid flow into the subretinal space until the retinopexy (photocoagulation or cryopexy) provides a permanent seal. For complex detachments involving PVR, silicone oil is often used. Commonly used viscosities of silicone oils include 1,000 and 5,000 centistokes. Silicone oils have a lower specific gravity (0.97 g/mL) than vitreous (1.005-1.008 g/mL), and as a result, they float in the vitreous cavity. Similarly, gases also float in the vitreous cavity due to their very low specific gravities (~0.001 g/mL) and they have a much greater buoyancy than silicone oils. Heavier silicone oils (HSOs) and perfluorocarbon liquids have been used for inferior retinal breaks because the lighter silicone oils and gases may be less effective tamponade for retinal breaks at these locations. Given the prevalence of PVR following retinal detachment and retinal detachment surgery, anti-inflammatory and immunosuppressive agents have been administered to control PVR and reduce the failure rates of PPV. Use of anti-inflammatory or immunosuppressive agents may be beneficial for subjects at higher risk of PVR.

Methotrexate (MTX) is an antineoplastic antimetabolite with immunosuppressant properties and inhibits enzymes requiring folate as a cofactor, including enzymes involved in nucleotide biosynthesis necessary for DNA replication. MTX has been used to treat chronic inflammatory and fibrotic conditions. In ophthalmology, MTX has been used to treat uveitis, pemphigoids, scleritis and episcleritis, and primary intraocular lymphoma. Studies of intravitreal MTX administration following retinal reattachment surgery show promise in reducing the incidence of retinal detachment following surgery (Benner et al., BMJ Open Ophth., 2019; 4:e000293; Sadaka et al., Clinical Ophthalmology, 2016; 10:1811-1817). Desirable are formulations of MTX for treating PVR following retinal detachment, particularly for cases when silicone oil is used as the preferred tamponade agent, as well as for treating other ocular disorders amenable to treatment with MTX, such as intraocular lymphoma and intraocular inflammatory conditions.

3. SUMMARY

The present disclosure provides a composition comprising methotrexate (MTX), and a density enhancing agent. In some embodiments, the composition is characterized by a transit time of less than 10 min through a silicone oil (SiO) of 1 cm depth. In some embodiments, the SiO is SiO used in treatment of retinal detachment. In some embodiments, the SiO is SiO having a viscosity of at least 1000 centistoke, e.g., polydimethyl siloxane having viscosity of 1000 centistoke. In some embodiments, the SiO is SiO having a viscosity of about 5000 centistoke. In some embodiments, the SiO is polydimethyl siloxane having a viscosity of about 5000 centistoke.

In some embodiments, the density enhancing agent is selected from sucrose, trehalose, glucose, carbomer (Carbopol®), polyvinyl acetate, polyvinyl alcohol (PVA), polyvinylpyrrolidone (PVP), carboxymethylcellulose, hydroxypropyl methylcellulose, hydroxypropyl cellulose, hydroxylethyl cellulose, polyethylene glycol (PEG), glycerol, poly(lactide) (PLA), poly(lactide-co-glycolide) (PLGA), polyglycolide (PGA), polyhydroxybutyric acid, polycaprolactone, polyvalerolactone, polyphosphazene, polyorthoester, cyclodextrin, and mixtures thereof. In some embodiments, the density enhancing agent is used in an appropriate amount to provide the desired density. In some embodiments, the density of the composition is $1.01 \text{ g/cm}^3$ or greater. In some embodiments, the density of the composition is about $1.01 \text{ g/cm}^3$ to about $1.08 \text{ g/cm}^3$.

In some embodiments, the composition further comprises a surfactant. In some embodiments, the surfactant is a non-ionic surfactant. In some embodiments, the surfactant can enhance the dispersion of the MTX in the aqueous phase. In some embodiments, the surfactant is selected from polyoxyethylene (20) sorbitan monolaurate (Tween® 20), polyoxyethylene (20) sorbitan monopalmitate (Tween® 40), polyoxyethylene (20) sorbitan monostearate (Tween® 60), polyoxyethylene (20) sorbitan mono-oleate (Tween® 80), polyoxyethylene (20) sorbitan tristearate (Tween® 65), polyoxyethylene (20) sorbitan tri-oleate (Tween® 85), sorbitan trioleate (Span® 85), sorbitan monopalmitate (Span® 40), sorbitan monostearate (Span® 60), sorbitan mono-oleate (Span® 80), and sorbitan tristearate (Span® 65). In some embodiments, the surfactant is Tween® 20 (polysorbate 20) or Tween® 80 (polysorbate 80). In some embodiments, the surfactant is present at about 0.001 w/v to about 0.05% w/v.

In some embodiments, the composition includes a buffering agent. In some embodiments, the buffering agent is a pharmaceutically acceptable buffering agent, in particular for intravitreal administration. In some embodiments, the buffering agent is borate, phosphate, bicarbonate, carbonate, citrate, tetraborate, biphosphate, tromethamine, hydroxy-ethyl morpholine, or THAM (trishydroxymethylamino-methane).

In some embodiments, the composition has a pH of about 6 to 8. In some embodiments, the composition has a pH of about 6.5 to about 7.5. In some embodiments, the composition has a pH appropriate for intravitreal administration.

In some embodiments, the composition has MTX, or a pharmaceutical salt thereof, at a concentration of about 2 mg/mL to about 20 mg/mL. In some embodiments, the MTX, or a pharmaceutical salt thereof, is at a concentration of about 5 mg/mL to about 15 mg/mL.

In another aspect, the MTX composition is used to prevent or to reduce the risk of or to treat proliferative vitreoretinopathy (PVR). In some embodiments, a method of preventing or reducing the risk of or treating PVR comprises administering to an eye of a subject in need thereof a therapeutically effective amount of a composition described herein. In some embodiments, the composition is administered intravitreally.

In some embodiments, the subject for treatment with the composition has suffered trauma to the eye. In some embodiments, the subject has suffered a retinal detachment. In some embodiments, the eye of the subject for treatment has been treated with vitreoretinal surgery for retinal detachment. In some embodiments, the retinal detachment is primary retinal detachment or secondary retinal detachment. In some embodiments, the retinal detachment is rhegmatogenous retinal detachment.

In some embodiments, the eye of the subject for treatment is treated or has been treated by administration of silicone oil (SiO) into the posterior segment, such as a tamponade for retinal detachment. In some embodiments, the MTX composition is administered by intravitreal injection into the SiO in the vitreous cavity. In some embodiments, the MTX composition is co-administered with the SiO administered to treat the retinal detachment. In some embodiments, the SiO has a viscosity of at least 1000 centistoke. In some embodiments, the SiO has a viscosity of about 1000 centistoke or about 5000 centistoke.

In some embodiments, the dose of MTX administered is a therapeutically effective amount at a frequency and duration to prevent or reduce the risk of or to treat PVR. In some embodiments, the dose of MTX administered is about 50 µg to about 600 µg. In some embodiments, the dose of MTX administered is about 400 µg. In some embodiments, the composition is administered once per day, twice per week, or once a week.

In some embodiments, the subject is treated with the composition for at least one week, at least two weeks, at least three weeks, at least one month, at least 6 months, at least 9 months, or for 1 year. In some embodiments where the subject has been treated with a gas or SiO as a tamponade, the subject is treated with the composition for the duration of treatment with the gas in the eye or until removal of the SiO.

In some embodiments, the subject for treatment with the composition has one or more risk factors for developing PVR. In some embodiments, the subject for treatment has a prior history of one or more of the following conditions: chronic ocular inflammation, infectious retinitis, multiple retinal detachments, large retinal breaks or giant retinal tears, multiple retinal breaks, ocular trauma, retinal detachment associated with vitreous hemorrhage, choroidal detachment, and combinations thereof. In some embodiments, the subject for treatment has had vitreous or subretinal hemorrhage, excessive cryotherapy, pigment release during endodrainage, or combinations thereof.

In some embodiments, the compositions herein are also useful for treating other diseases, disorders, or conditions that would benefit from intravitreal administration of methotrexate.

In some embodiments, the compositions herein are used to treat intraocular lymphoma. In some embodiments, a method of treating intraocular lymphoma comprises administering intravitreally to an eye of a subject with intraocular lymphoma a therapeutically effective amount of a composition disclosed herein, including the exemplary formulations disclosed herein.

In some embodiments, the intraocular lymphoma to be treated is primary vitreoretinal lymphoma (PVRL). In some embodiments, the intraocular lymphoma (e.g., PVRL) is accompanied by cerebral nervous system lymphoma (PCNSL). In some embodiments, the intraocular lymphoma is diffuse large B-cell lymphoma.

In some embodiments, the compositions herein are used to treat intraocular inflammation. In some embodiments, a method of treating intraocular inflammation comprises administering intravitreally to a subject with intraocular inflammation a therapeutically effective amount of a composition disclosed herein. In some embodiments, the inflammatory diseases, disorders, or conditions for treatment with the MTX compositions herein include, among others, uveitis, for example pan uveitis, intermediate uveitis, and posterior uveitis, particularly non-infectious posterior uveitis; cystoid macular edema (CME); macular edema, for example accompanying uveitis or diabetic macular edema; choroidal neovascularization; and prosthetic membranopathy.

In some embodiments, the dose of MTX administered is a therapeutically effective amount at a frequency and duration to prevent or reduce the risk of or to treat intraocular lymphoma or to prevent or reduce the risk of or to treat intraocular inflammation.

In some embodiments for treating intraocular lymphoma or intraocular inflammation, the MTX composition is administered once every 4 weeks (month), once every two weeks, once a week, two times a week, three times a week, or four times a week to treat the intraocular lymphoma or intraocular inflammation.

In some embodiments for treating intraocular lymphoma or intraocular inflammation, the treatment regimen includes an induction phase, and optionally a consolidation phase, and/or a maintenance phase.

In some embodiments, the induction phase is administration of the MTX composition two times a week, three times a week, up to four times a week.

In some embodiments, the consolidation phase, when present, comprises administration once a week or two times a week.

In some embodiments, the maintenance phase, when present, comprises administration once every two weeks, once every three weeks, or once every month.

In another aspect, the present disclosure provides kits comprising the MTX compositions described herein. In some embodiments of the kits, the MTX composition can be provided as multi-dose vial or single dose vial. In some embodiments, the MTX composition can be in dry form, which is reconstituted with an appropriate solvent for preparing the composition for administration.

4. BRIEF DESCRIPTION OF THE DRAWINGS

FIG. 1 illustrates the properties of formulations F1, F2, and F3 in transiting through polydimethyl siloxane 5000 centistoke oil to reach the bottom of the silicone oil layer, i.e., oil-buffer interface, of a non-miscible silicone oil/buffer mixture.

5. DETAILED DESCRIPTION

5.1. Methotrexate Compositions

The present disclosure provides compositions of methotrexate (MTX), or a pharmaceutically acceptable salt thereof, for preventing, reducing the risk of, or treating proliferative vitreoretinopathy (PVR), intraocular lymphoma, or intraocular inflammation.

In some embodiments, the composition of MTX is used as prophylaxis against PVR, such as following retinal detachment surgery. In some embodiments, the present compositions provide sufficient rate of transit through silicone oil (SiO) used in retinal detachment surgery to deliver MTX in a therapeutically effective amount to prevent, reduce the risk of, or treat PVR.

In some embodiments, the composition of MTX is used to treat intraocular lymphoma, such as primary vitreoretinal lymphoma (PVRL).

In some embodiments, the compositions of MTX are used to treat intraocular inflammation, such as uveitis; cystoid macular edema (CME) or diabetic macular edema; choroidal neovascularization; or prosthetic membranopathy.

In reference to the present disclosure and the detailed description that follow, the singular forms "a", "an" and "the" include plural referents unless the context clearly indicates otherwise. Thus, for example, reference to "a compound" refers to more than one compound.

Also, the use of "or" means "and/or" unless stated otherwise. Similarly, "comprise," "comprises," "comprising," "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

As used herein, the term "treating" or "treatment" of a disease, disorder, or syndrome, as used herein, includes (i) preventing the disease, disorder, or syndrome from occurring in a subject, i.e., causing the clinical symptoms of the disease, disorder, or syndrome not to develop in an animal that may be exposed to or predisposed to the disease, disorder, or syndrome but does not yet experience or display symptoms of the disease, disorder, or syndrome; (ii) inhibiting the disease, disorder, or syndrome, i.e., arresting its development; and (iii) relieving the disease, disorder, or syndrome, i.e., causing regression of the disease, disorder, or syndrome. As is known in the art, adjustments for systemic versus localized delivery, age, body weight, general health, sex, diet, time of administration, drug interaction and the severity of the condition may be necessary, and is ascertainable by one of ordinary skill in the art.

As used herein, the term "prophylactic treatment" refers to a treatment administered to a subject who does not display signs or symptoms of a disease, pathology, or medical disorder, or displays only early signs or symptoms of a disease, pathology, or disorder, for the purpose of diminishing, preventing, or decreasing the risk of developing the disease, pathology, or medical disorder. A prophylactic treatment functions as a preventative treatment against a disease or disorder.

As used herein, the term "therapeutically effective amount" means any amount which, as compared to a corresponding subject who has not received such amount, results in improved treatment, healing, prevention, or amelioration of a disease or disorder, or a decrease in the rate of advancement of a disease or disorder, and also includes amounts effective to enhance normal physiological function.

As used herein, the term "pharmaceutically acceptable" refers to those compounds, biologic agents, materials, compositions and/or dosage forms, which are, within the scope of sound medical judgment, suitable for administration to a subject, e.g., a mammal or human, without excessive toxicity, irritation allergic response and other problem complications commensurate with a reasonable benefit/risk ratio.

In one aspect, the present disclosure provides a composition comprising MTX, or a pharmaceutically acceptable salt thereof, and a density enhancing agent. In some embodiments, the density enhancing agent is present in an amount effective to provide a transit rate of less than 10 min in 1 ml of silicone oil (SiO). As used herein, a "transit rate" refers to the time in which the MTX composition when applied to SiO layer separated from a non-miscible aqueous layer, preferably phosphate buffered saline (PBS), reaches the interface of the SiO and aqueous layer. In some embodiments, where the composition has a higher density than the density of the SiO, the transit rate can be referred to as the "sink rate." In some embodiments, the transit or sink rate of the composition is less than 10 min, less than 8 min, less than 7 min, less than 6 min, or less than 5 min in 1 ml of SiO having a depth of 1 cm. In some embodiments, the transit rate or sink rate of the composition is measured in SiO used as a tamponade for treating retinal detachment.

In some embodiments, the SiO has a lower density than water. In these SiOs, the SiO layer floats on top of an aqueous layer, and the MTX composition sinks in the SiO to the interface of the SiO and aqueous layer.

In some embodiments, the transit rate or sink rate is in SiO having a viscosity of at least 1000 centistoke. In some embodiments, the SiO has a viscosity of about 1000 centistoke. In some embodiments, the SiO having a viscosity of 1000 centistoke is polydimethyl siloxane 1000 centistoke oil.

In some embodiments, the transit rate or sink rate is in SiO having a viscosity of about 5000 centistoke. In some embodiments, the SiO having a viscosity of 5000 centistoke is polydimethyl siloxane 5000 centistoke oil.

In some embodiments, the density of the MTX composition is higher than the density of the SiO to provide an appropriate transit rate or sink rate. In some embodiments, the density of the composition is at least about 1.01 $g/cm^3$, at least about 1.02 $g/cm^3$, at least about 1.03 $g/cm^3$, at least about 1.04 $g/cm^3$, at least about 1.05 $g/cm^3$, at least about 1.06 $g/cm^3$, at least about 1.07 $g/cm^3$, at least about 1.08 $g/cm^3$, at least about 1.09 $g/cm^3$, at least about 1.10 $g/cm^3$, at least about 1.11 $g/cm^3$, at least about 1.12 $g/cm^3$, at least about 1.13 $g/cm^3$, at least about 1.14 $g/cm^3$, at least about 1.15 $g/cm^3$, at least about 1.20 $g/cm^3$, or at least about 1.25 $g/cm^3$ at 20° C.

In some embodiments, the density of the MTX composition is about 1.01 to about 1.2 $g/cm^3$, about 1.02 $g/cm^3$ to about 1.2 $g/cm^3$, about 1.03 $g/cm^3$ to about 1.2 $g/cm^3$, about 1.04 $g/cm^3$ to about 1.2 $g/cm^3$, about 1.05 $g/cm^3$ to about 1.2 $g/cm^3$, about 1.06 $g/cm^3$ to about 1.2 $g/cm^3$, about 1.07 $g/cm^3$ to about 1.2 $g/cm^3$, about 1.08 $g/cm^3$ to about 1.2 $g/cm^3$, about 1.09 $g/cm^3$ to about 1.2 $g/cm^3$, about 1.10 $g/cm^3$ to about 1.2 $g/cm^3$, about 1.11 $g/cm^3$ to about 1.2 $g/cm^3$, about 1.12 $g/cm^3$ to about 1.2 $g/cm^3$, about 1.13 g/cm³ to about 1.2 g/cm³, about 1.14 g/cm³ to about 1.2 g/cm³, about 1.15 g/cm³ to about 1.2 g/cm³, about 1.16 g/cm³ to about 1.2 g/cm³, about 1.17 g/cm³ to about 1.2 g/cm³, about 1.18 g/cm³ to about 1.2 g/cm³, or about 1.19 g/cm³ to about 1.2 g/cm³ at 20° C. In some embodiments, the composition has a density of about 1.01 g/cm³ to about 1.08 g/cm³ at 20° C.

In some embodiments, the density of the composition is about 1.01 to about 1.25 g/cm³ at 20° C. In some embodiments, the density of the composition is about 1.02 to about 1.2 g/cm³ at 20° C. In some embodiments, the density of the composition is about 1.03 to about 1.15 g/cm³ at 20° C. In some embodiments, the density of the composition is about 1.04 to about 1.1 g/cm³ at 20° C.

In some embodiments, the density of the composition is about 1.01 g/mL, about 1.02 g/cm³, about 1.03 g/cm³, about 1.04 g/cm³, about 1.05 g/cm³, about 1.06 g/cm³, about 1.07 g/cm³, about 1.08 g/cm³, about 1.09 g/cm³, about 1.10 g/cm³, about 1.11 g/cm³, about 1.12 g/cm³, about 1.13 g/cm³, about 1.14 g/cm³, about 1.15 g/cm³, about 1.16 g/cm³, about 1.17 g/cm³, about 1.18 g/cm³, about 1.19 g/mL, about 1.2 g/cm³, about 1.21 g/cm³, about 1.22 g/cm³, about 1.23 g/cm³, about 1.24 g/cm³, or about 1.25 g/cm³ at 20° C.

In some embodiments, the SiO is heavy silicone oil (HSO), which refers to SiO that has a higher density than the density of water. In such embodiments, the aqueous layer floats on top of the HSO layer. In some embodiments, the MTX composition is formulated to have a lower density than the density of HSO, thus allowing the MTX composition to float from the SiO to the interface of the SiO and aqueous layer. In some embodiments, the transit rate of the MTX composition is less than 10 min in 1 ml of HSO at a depth of 1 cm. In some embodiments, the transit rate of the MTX composition is less than 8 min, less than 7 min, less than 6 min, or less than 5 min in 1 ml of HSO having a depth of 1 cm. In some embodiments, the MTX composition is applied to the bottom of the SiO layer 1 cm away from the interface of the HSO and the aqueous layer to assess the transit rate.

In some embodiments, the HSO is Oxane HD (mixture of 5700-centistoke SiO and RMN-3, a partially fluorinated olefin; density of 1.02 g/cm³ and a viscosity of 3,300-3,500 mPas at 25° C.), Densiron 68 (mixture of perfluorohexyloctane (F6H8) and 5,000-centistoke silicone oil; density 1.06 g/cm³; viscosity 1400 mPas at 25° C.), or HSV-45 3000. In some embodiments, the HSO is perfluorocarbon liquids (PFCLs) or semifluorinated alkanes, such as perfluorohexyloctane (F6H8; density of 1.331 g/cm³). PFCLs include perfluoro-n-octane (C8F18; density of 1.759 g/cm³) and perfluorodecalin (C10F18). The specific gravity of these SiOs can range from 1.7 g/mL to more than 2.0 g/mL.

In some embodiments where HSO is used, the density of the MTX composition is lower than the density of the HSO. In some embodiments, the density of the composition is less than about 2.0 g/cm³, less than about 1.8 g/cm³, less than about 1.6 g/cm³, less than about 1.5 g/cm³, less than about 1.4 g/cm³, less than about 1.3 g/cm³, less than about 1.2 g/cm³, less than about 1.19 g/cm³, less than about 1.18 g/cm³, less than about 1.17 g/cm³, less than about 1.16 g/cm³, less than about 1.15 g/cm³, less than about 1.14 g/cm³, less than about 1.13 g/cm³, less than about 1.12 g/cm³, less than about 1.11 g/cm³, less than about 1.10 g/cm³, less than about 1.09 g/cm³, less than about 1.08 g/cm³, less than about 1.07 g/cm³, less than about 1.06 g/cm³, less than about 1.05 g/cm³, less than about 1.04 g/cm³, less than about 1.03 g/cm³, or less than about 1.02 g/cm³.

In some embodiments, the density of the composition is about 2.0 g/cm³ to about 1.01 g/cm³, about 1.8 g/cm³ to about 1.01 g/cm³, about 1.6 g/cm³ to about 1.01 g/cm³, about 1.5 g/cm³, to about 1.01 g/cm³, about 1.4 g/cm³ to about 1.01 g/cm³, about 1.3 g/cm³ to about 1.01 g/cm³, about 1.2 g/cm³ to about 1.01 g/cm³, about 1.19 g/cm³ to about 1.01 g/cm³, about 1.18 g/cm³ to about 1.01 g/cm³, about 1.17 g/cm³ to about 1.01 g/cm³, about 1.16 g/cm³ to about 1.01 g/cm³, about 1.15 g/cm³, to about 1.01 g/cm³, about 1.14 g/cm³ to about 1.01 g/cm³, about 1.13 g/cm³ to about 1.01 g/cm³, about 1.12 g/cm³ to about 1.01 g/cm³, about 1.11 g/cm³ to about 1.01 g/cm³, about 1.10 g/cm³ to about 1.01 g/cm³, about 1.09 g/cm³ to about 1.01 g/cm³, about 1.08 g/cm³ to about 1.01 g/cm³, about 1.07 g/cm³ to about 1.01 g/cm³, about 1.06 g/cm³ to about 1.01 g/cm³, about 1.05 g/cm³ to about 1.01 g/cm³, about 1.04 g/cm³ to about 1.01 g/cm³, or about 1.03 g/cm³ to about 1.01 g/cm³.

In some embodiments, where a combination of an oil having a density lower than water and an oil having a density higher than water are used as a tamponade, the MTX composition has a density greater than the oil having lower density than water and a density lower than the oil having a higher density than water. The MTX composition having the appropriate density can be selected based on the guidance provide herein. In some embodiments, compositions having the appropriate density in the applicable ranges describe above can be used.

In certain embodiments, the composition comprises a density enhancing agent to provide an appropriate density to impart a desired transit rate or sink rate. In some embodiments, the density enhancing agent is sucrose, trehalose, glucose, carbomer (Carbopol®), polyvinyl acetate, polyvinyl alcohol (PVA), polyvinylpyrrolidone (PVP), carboxymethylcellulose, hydroxypropyl methylcellulose, hydroxypropyl cellulose, hydroxylethyl cellulose, polyethylene glycol (PEG), glycerol, poly(lactide) (PLA), poly(lactide-co-glycolide) (PLGA), polyglycolide (PGA), polyhydroxybutyric acid, polycaprolactone, polyvalerolactone, polyphosphazene, polyorthoester, cyclodextrin, or mixtures thereof. In some embodiments, a preferred density enhancing agent is sucrose or PEG 4000.

In some embodiments, the density enhancing agent comprises sucrose. In some embodiments, the composition comprises sucrose at a concentration of about 0.5% w/v to about 20% w/v; about 1% w/v to about 20% w/v, 2% w/v to about 20% w/v, about 3% w/v to about 20% w/v, about 4% w/v to about 20% w/v, about 5% w/v to about 20% w/v, about 6% w/v to about 20% w/v, about 7% w/v to about 20% w/v, about 8% w/v to about 20% w/v, about 9% to w/v about 20% w/v, about 10% w/v to about 20% w/v, about 11% w/v to about 20% w/v, about 12% w/v to about 20% w/v, about 13% w/v to about 20%, about 14% w/v to about 20%, about 15% w/v to about 20%, or about 16% w/v to about 20%.

In some embodiments, the composition comprises sucrose at a concentration of about 0.5% w/v to about 18% w/v, about 1% w/v to about 17%, w/v 2% w/v to about 16% w/v, about 3% w/v to about 15% w/v, about 4% w/v to about 14% w/v, about 5% w/v to about 1% w/v, about 6% w/v to about 13% w/v, about 7% to about 12% w/v, or about 8% to about 11% w/v. In some embodiments, the composition comprises sucrose at a concentration of about 7% w/v to about 9% w/v, preferably about 7.7% w/v.

In some embodiments, the composition comprises sucrose at a concentration of about 0.5% w/v, about 0.6% w/v, about 0.7% w/v, about 0.8% w/v, about 0.9% w/v, about 1% w/v, about 2% w/v, about 3% w/v, about 4% w/v, about 5% w/v, about 6% w/v, about 7% w/v, about 8% w/v, about 9% w/v, about 10% w/v, about 11% w/v, about 12% w/v, about 13% w/v, about 14% w/v, about 15% w/v, about 16% w/v, about 17% w/v, about 18% w/v, about 19% w/v, or about 20% w/v. In some embodiments, the composition has sucrose at a concentration of about 7.5% w/v, 8.5% w/v, or about 9.5% w/v.

In some embodiments, the density enhancing agent comprises polyethylene glycol (PEG). In some embodiments, the PEG is PEG 400 to PEG 20000. In some embodiments, the PEG is PEG 400, PEG 500, PEG 600, PEG 700, PEG 800, PEG 900, PEG 1000, PEG 1100, PEG 1200, PEG 1300, PEG 1400, PEG 1450, PEG 1500, PEG 1600, PEG 1700, PEG 1800, PEG 1900, PEG 2000, PEG 2100, PEG 2200, PEG 2300, PEG 2400, PEG 2500, PEG 2600, PEG 2700, PEG 2800, PEG 2900, PEG 3000, PEG 3250, PEG 3350, PEG 3500, PEG 3750, PEG 4000, PEG 4250, PEG 4500, PEG 4750, PEG 5000, PEG 5500, PEG 6000, PEG 6500, PEG 7000, PEG 7500, PEG 8000, or mixtures thereof. In some embodiments, the PEG is PEG 9000, PEG 10000, PEG 11000, PEG 12000, PEG 13000, PEG 14000, PEG 15000, PEG 16000, PEG 17000, PEG 18000, PEG 19000, PEG 20000, or mixtures thereof. In a preferred embodiment, the PEG is PEG 4000.

In some embodiments, the composition comprises PEG at a concentration to provide sufficient density for the composition to have the transit rate or sink rate described herein. The densities of PEG solutions of different molecular weights are available in the art (see, e.g., Gonzalez-Tello et al., J Chem Eng Data, 1994; 39:611-614; Regupahti et al., J. Chem. Eng. Data, 2009; 54(3):1100-1106; publications incorporated herein by reference). For example, PEG 4000 at 50% w/v in water has a density of about 1.13 g/cm$^3$ at 20° C.

In some embodiments, the composition comprises PEG 4000 at a concentration of about 1% w/v to about 60% w/v, about 1% w/v to about 60% w/v, about 2% w/v to about 60% w/v, about 3% w/v to about 60% w/v, about 4% w/v to about 60% w/v, about 5% w/v to about 60% w/v, about 6% w/v to about 60% w/v, about 7% w/v to about 60% w/v, about 8% w/v to about 60% w/v, about 9% w/v to about 60% w/v, about 10% w/v to about 60% w/v, about 15% w/v to about 60% w/v, about 20% w/v to about 60% w/v, about 25% w/v to about 60% w/v, about 30% w/v to about 60% w/v, about 35% w/v to about 60% w/v, about 40% w/v to about 60% w/v, about 45% w/v to about 60%, about 50% w/v to about 60% w/v, or about 55% w/v to about 60% w/v.

In some embodiments, the composition comprises PEG 4000 at a concentration of about 1% w/v to about 60% w/v, about 1% w/v to about 55% w/v, about 2% w/v to about 50% w/v, about 3% w/v to about 45% w/v, about 4% w/v to about 40% w/v, about 5% w/v to about 35% w/v, about 6% w/v to about 30% w/v, about 7% w/v to about 28% w/v, about 8% w/v to about 26% w/v, about 9% w/v to about 24% w/v, about 10% w/v to about 22% w/v, or about 15% w/v to about 20% w/v. In some embodiments, the composition comprises PEG 4000 at a concentration of about 1% w/v to about 15% w/v, 12% w/v to about 14% w/v, 3% w/v to about 13% w/v, 4% w/v to about 12% w/v, 5% w/v to about 11% w/v, 6% w/v to about 10% w/v, or 7% w/v to about 9% w/v.

In some embodiments, the composition comprises PEG 4000 at a concentration of about 1% w/v, about 2% w/v, about 3% w/v, about 4% w/v, about 5% w/v, about 6% w/v, about 7% w/v, about 8% w/v, about 9% w/v, about 10% w/v, about 11% w/v, about 12% w/v, about 13% w/v, about 14% w/v, about 15% w/v, about 16% w/v, about 17% w/v, about 18% w/v, about 19% w/v, about 20% w/v, about 25% w/v, about 30% w/v, about 35% w/v, about 40% w/v, about 45% w/v, about 50% w/v, about 55% w/v, or about 60% w/v.

It is to be understood that while the description for the MTX composition herein uses sucrose or PEG 4000 as exemplary density enhancing agents, the appropriate concentration of other density enhancing agents to achieve the desired transit rate or sink rate and/or the desired density can be used in view of the knowledge in the art of the densities for the various density enhancing agents described herein.

In some embodiments, the MTX composition further comprises one or more surfactants. In some embodiments, the surfactant is a non-ionic surfactant. In some embodiments, the surfactant is suitable for intravitreal administration. In some embodiments, the surfactant is polyoxyethylene (20) sorbitan monolaurate (Tween® 20), polyoxyethylene (20) sorbitan monopalmitate (Tween® 40), polyoxyethylene (20) sorbitan monostearate (Tween® 60), polyoxyethylene (20) sorbitan mono-oleate (Tween® 80), polyoxyethylene (20) sorbitan tristearate (Tween® 65), polyoxyethylene (20) sorbitan tri-oleate (Tween® 85), sorbitan trioleate (Span® 85), sorbitan monopalmitate (Span® 40), sorbitan monostearate (Span® 60), sorbitan mono-oleate (Span® 80), sorbitan tristearate (Span® 65), or combinations thereof. In some embodiments, the surfactant is Tween® 20 (polysorbate 20) or Tween® 80 (polysorbate 80).

In some embodiments, the composition comprises a surfactant at about 0.001% w/v to about 0.5% w/v, about 0.002% w/v to about 0.5% w/v, about 0.004% w/v to about 0.5% w/v, about 0.006% w/v to about 0.5% w/v, about 0.008% w/v to about 0.5% w/v, about 0.010% w/v to about 0.5% w/v, about 0.012% w/v to about 0.5% w/v, about 0.014% w/v to about 0.5% w/v, about 0.016% w/v to about 0.5% w/v, about 0.018% w/v to about 0.5% w/v, about 0.02% w/v to about 0.5% w/v, about 0.03% w/v to about 0.5% w/v, about 0.04% w/v to about 0.5% w/v, about 0.05% w/v to about 0.5% w/v, about 0.06% w/v to about 0.5% w/v, about 0.07% w/v to about 0.5% w/v, about 0.08% w/v to about 0.5% w/v, about 0.1% w/v to about 0.5% w/v, about 0.12% w/v to about 0.5% w/v, about 0.14% w/v to about 0.5% w/v, about 0.16% w/v to about 0.5% w/v, about 0.18% w/v to about 0.5% w/v, about 0.2% w/v to about 0.5% w/v, about 0.3% w/v to about 0.5% w/v, or about 0.4% w/v to about 0.5% w/v. In some embodiments, the surfactant is present at 0.0015% w/v to about 0.05% w/v. In some embodiments, the surfactant is present at 0.01% w/v to 0.05% w/v. In some embodiments, the surfactant is present at 0.015% w/v to about 0.03% w/v.

In some embodiments, the composition has surfactant at about 0.001% w/v, about 0.002% w/v, about 0.004% w/v, about 0.006% w/v, about 0.008% w/v, about 0.010% w/v, about 0.012% w/v, about 0.014% w/v, about 0.016% w/v, about 0.018% w/v, about 0.02% w/v, about 0.03% w/v, about 0.04% w/v, about 0.05% w/v, about 0.06% w/v, about 0.07% w/v, about 0.08% w/v, about 0.1% w/v, about 0.12% w/v, about 0.14% w/v, about 0.16% w/v, about 0.18% w/v, about 0.2% w/v, about 0.22% w/v, about 0.24% w/v, about 0.26% w/v, about 0.28% w/v, about 0.3% w/v, about 0.32% w/v, about 0.34% w/v, about 0.36% w/v, about 0.38% w/v, about 0.4% w/v, about 0.42% w/v, about 0.44% w/v, about 0.46% w/v, about 0.48% w/v, or about 0.5% w/v.

In some embodiments, the composition includes a preservative, particularly a pharmaceutically acceptable preservative for intravitreal injection. In some embodiments, the preservative is benzyl alcohol. In some embodiments, the composition is free of preservatives.

In some embodiments, the composition further comprises a buffering agent. In some embodiments, the buffering agent is a pharmaceutically acceptable buffering agent, in particular a buffering agent suitable for intravitreal administration. In some embodiments, the buffering agent is borate, phosphate, bicarbonate, carbonate, citrate, tetraborate, biphosphate, tromethamine, hydroxyethyl morpholine, or THAM (trishydroxymethylamino-methane). In some embodiments, the buffering agent is phosphate.

In some embodiments, the buffering agent is present in a sufficient amount to provide buffering capacity to the composition. In some embodiments, the buffering agent is present at a concentration of about 0.005 mM to about 5 mM, about 0.01 mM to about 4 mM, about 0.02 mM to about 3 mM, about 0.03 mM to about 2 mM, about 0.04 mM to about 1.5 mM, about 0.05 mM to about 1 mM, or about 0.1 mM to about 0.8 mM.

In some embodiments, the buffering agent is present at a concentration of about 0.005 mM, 0.01 mM, 0.02 mM, 0.03 mM, 0.04 mM, 0.05 mM, 0.1 mM, 0.2 mM, 0.3 mM, 0.4 mM, 0.5 mM, 0.6 mM, 0.7 mM, 0.8 mM, 0.9 mM, 1 mM, 2 mM, 3 mM, 4 mM, 5 mM or more as needed.

In some embodiments, the pH of the composition is about 5.5 to about 8.5. In some embodiments, the pH is about 6 to about 8, or about 6.5 to about 7.5. In some embodiments, the composition has a pH of about 5.5, about 6.0, about 6.5, about 7, about 7.5 or about 8. Preferably, the pH of the composition is approximate pH of the vitreous in the eye.

In some embodiments, the MTX is present in the composition at a concentration that when administered is sufficient to prevent or reduce the risk of or treat a disease, disorder, or conditions disclosed herein. In some embodiments, the MTX is present in the composition at a concentration sufficient to prevent or reduce the risk of or treat PVR. In some embodiments, the MTX is present in the composition at a concentration sufficient to prevent or reduce the risk of or treat intraocular lymphoma. In some embodiments, the MTX is present in the composition at a concentration sufficient to prevent or reduce the risk of or treat intraocular inflammation. Methotrexate is also known by its chemical names N-[4-[[(2,4-diamino-6-pteridinyl)methyl]methylamino]benzoyl]-L-glutamic acid and 4-amino-10-methylfolic acid. In some embodiments, the MTX in composition is present in an amount such that intravitreal administration provides a therapeutically effective dose, including a prophylactically effective dose.

In some embodiments, the MTX, or a pharmaceutically acceptable salt thereof, is present at about 2 mg/mL to about 20 mg/mL. In some embodiments, the MTX, or a pharmaceutically acceptable salt thereof, is present at about 3 mg/mL to about 20 mg/mL, about 4 mg/mL to about 20 mg/mL, about 5 mg/mL to about 20 mg/mL, about 6 mg/mL to about 20 mg/mL, about 7 mg/mL to about 20 mg/mL, about 8 mg/mL to about 20 mg/mL, about 9 mg/mL to about 20 mg/mL, about 10 mg/mL to about 20 mg/mL, about 11 mg/mL to about 20 mg/mL, about 12 mg/mL to about 20 mg/mL, about 13 mg/mL to about 20 mg/mL, about 14 mg/mL to about 20 mg/mL, about 15 mg/mL to about 20 mg/mL, about 16 mg/mL to about 20 mg/mL, or about 18 mg/mL to about 20 mg/mL.

In some embodiments, the MTX, or a pharmaceutically acceptable salt thereof, is present at about 2 mg/mL to about 19 mg/mL, about 3 mg/mL to about 18 mg/mL, about 4 mg/mL to about 18 mg/mL, about 5 mg/mL to about 17 mg/mL, about 6 mg/mL to about 16 mg/mL, about 7 mg/mL to about 15 mg/mL, about 8 mg/mL to about 14 mg/mL, about 9 mg/mL to about 13 mg/mL, about 10 mg/mL to about 12 mg/mL. In some embodiments, the MTX, or a pharmaceutically acceptable salt thereof, is present at about 5 mg/ml to about 12 mg/mL, 6 mg/mL to about 11 mg/mL, or about 7 mg/mL to about 10 mg/mL.

In some embodiments, the MTX, or a pharmaceutically acceptable salt thereof, is present at about 2 mg/mL, about 3 mg/mL, about 4 mg/mL, about 5 mg/mL, about 6 mg/mL, about 7 mg/mL, about 8 mg/mL, about 9 mg/mL, about 10 mg/mL, about 11 mg/mL, about 12 mg/mL, about 13 mg/mL, about 14 mg/mL, about 15 mg/mL, about 16 mg/mL, about 18 mg/mL, or about 20 mg/mL. Preferably, the MTX is present at about 8 mg/mL.

In some embodiments, the MTX is present in the composition as a pharmaceutically acceptable salt or as esters of MTX. Pharmaceutically acceptable salts can be selected from, but are not limited to, alkali metal salts such as sodium or potassium, alkaline earth salts or an ammonium salt (all of which are herein referred to as a pharmaceutically acceptable salts). In some embodiments, methotrexate refers to methotrexate disodium. Methotrexate also includes acetylated forms, benzhydryl-sulfinylacetic acid forms, sulfone forms, hydroxylated forms, polymorphic forms, analogs, derivatives, cogeners, prodrugs, metabolic acids and compounds made by mixtures thereof. In some embodiments, the methotrexate also includes individual enantiomers or racemic mixtures of methotrexate.

In some embodiments, the composition has an osmolarity that is compatible with its use in treating a disease, disorder, or condition disclosed herein. In some embodiments, the osmolarity of the composition is compatible with intravitreal use. In some embodiments, the composition has an osmolarity of about 200 to about 1000 mOsm/L or about 200 to about 500 mOsm/L, or any specific value within said ranges, for example, 200 mOsm/L, 210 mOsm/L, 220 mOsm/L, 230 mOsm/L, 240 mOsm/L, 250 mOsm/L, 260 mOsm/L, 270 mOsm/L, 280 mOsm/L, 290 mOsm/L, 300 mOsm/L, 310 mOsm/L, 320 mOsm/L, 330 mOsm/L, 340 mOsm/L, 350 mOsm/L, 360 mOsm/L, 370 mOsm/L, 380 mOsm/L, 390 mOsm/L, or 400 mOsm/L. In a particular embodiment, the ophthalmic formulations are adjusted with a tonicity agent to an osmolarity in the range of about 250 to about 450 mOsm/L, or about 300 to about 400 mOsm/L. Preferably, the osmolarity of the composition is about 350±50 mOsm/L.

In some embodiments, the compositions can have one or more tonicity agents, which can be used to adjust the tonicity of the composition, for example, to the tonicity appropriate for intravitreal use. Suitable tonicity agents include, by way of example and not limitation, dextrans (e.g., dextran 40 or 70), dextrose, glycerin, potassium chloride, propylene glycol, and sodium chloride. Equivalent amounts of one or more salts made up of cations, such as potassium, ammonium; and anions such as chloride, citrate, ascorbate, borate, phosphate, bicarbonate, sulfate, thiosulfate, bisulfate; the salts sodium bisulfate and ammonium sulfate, can also be used. The amount of tonicity agent can vary, depending on the particular agent to be added.

In some embodiments, the MTX composition comprises the following:
  Methotrexate: 2 mg/mL to about 20 mg/mL; and
  Sucrose: 0.5% w/v to about 20% w/v.
In some embodiments, the MTX composition comprises the following:
  Methotrexate: 5 mg/mL to about 15 mg/mL; and
  Sucrose: 4% w/v to about 15% w/v.

In some embodiments, the MTX composition comprises the following:

Methotrexate: 2 mg/mL to about 20 mg/mL; and
PEG 4000: 1% w/v to about 60% w/v.

In some embodiments, the MTX composition comprises the following:

Methotrexate: 5 mg/mL to about 15 mg/mL; and
PEG 4000: 4% w/v to about 15% w/v.

In some embodiments, each of the above compositions further includes a surfactant. In some embodiments, any of the surfactants disclosed herein can be used. In some embodiments, the surfactant is polyoxyethylene (20) sorbitan monolaurate (Tween® 20), polyoxyethylene (20) sorbitan monopalmitate (Tween® 40), polyoxyethylene (20) sorbitan monostearate (Tween® 60), polyoxyethylene (20) sorbitan mono-oleate (Tween® 80), polyoxyethylene (20) sorbitan tristearate (Tween® 65), polyoxyethylene (20) sorbitan tri-oleate (Tween® 85), and sorbitan trioleate (Span® 85). sorbitan monopalmitate (Span® 40), sorbitan monostearate (Span® 60), sorbitan mono-oleate (Span® 80), or sorbitan tristearate (Span® 65). In some embodiments, the surfactant is Tween® 20 or Tween® 80.

In some embodiments, the MTX composition comprises the following:

Methotrexate: 2 mg/mL to about 20 mg/mL;
Sucrose: 0.5% w/v to about 20% w/v; and
Surfactant: 0.001% to about 0.5% w/v.

In some embodiments, the MTX composition comprises the following:

Methotrexate: 5 mg/mL to about 15 mg/mL;
Sucrose: 4% w/v to about 15% w/v;
Surfactant: 0.010% to about 0.05% w/v.

In some embodiments, the MTX composition comprises the following:

Methotrexate: 2 mg/mL to about 20 mg/mL; and
PEG 4000: 1% w/v to about 60% w/v; and
Surfactant: 0.001% to about 0.5% w/v.

In some embodiments, the MTX composition comprises the following:

Methotrexate: 5 mg/mL to about 15 mg/mL;
PEG 4000: 4% w/v to about 15% w/v; and
Surfactant: 0.010% to about 0.05% w/v.

In some embodiments, the surfactant in the above embodiments is Tween® 20, also referred to as polysorbate 20. In some embodiment, the surfactant in the above embodiments is Tween® 80, also referred to as polysorbate 80.

In some embodiments, the MTX composition has the following formulation (F1):

| Component | Concentration |
| --- | --- |
| Methotrexate | 8 mg/mL |
| Sucrose | 8% w/v |
| Sodium phosphate dibasic dihydrate | 0.142% w/v |
| 1M NaOH/HCl | pH adjusted to 7.4 ± 0.2 |
| Final volume | 1 mL |

In some embodiments, the MTX composition has the following formulation (F2):

| Component | Concentration |
| --- | --- |
| Methotrexate | 8 mg/mL |
| Polyethylene Glycol 4000 | 7.5% w/v |
| Sodium phosphate dibasic dihydrate | 0.142% w/v |

-continued

| Component | Concentration |
| --- | --- |
| 1M NaOH/HCl | pH adjusted to 7.4 ± 0.2 |
| Final volume | 1 mL |

In some embodiments, the MTX composition has the following formulation (F73):

| Component | Concentration |
| --- | --- |
| Methotrexate | 8 mg/mL |
| NaCl | 0.9% w/v |
| Final volume | 1 mL |

In some embodiments, the MTX composition has the following formulation (F4):

| Component | Concentration |
| --- | --- |
| Methotrexate | 8 mg/mL |
| Sucrose | 8% w/v |
| Tween ® 20 | 0.015% w/v |
| Sodium phosphate dibasic dihydrate | 0.142% w/v |
| 1M NaOH/HCl | pH adjusted to 7.4 ± 0.2 |
| Final volume | 1 mL |

In some embodiments, the MTX composition has the following formulation (F5):

| Component | Concentration |
| --- | --- |
| Methotrexate | 8 mg/mL |
| Sucrose | 8% w/v |
| Tween ® 20 | 0.03% w/v |
| Sodium phosphate dibasic dihydrate | 0.142% w/v |
| 1M NaOH/HCl | pH adjusted to 7.4 ± 0.2 |
| Final volume | 1 mL |

In some embodiments, the MTX composition has the following formulation (F6):

| Component | Concentration |
| --- | --- |
| Methotrexate | 8 mg/mL |
| Sucrose | 8% w/v |
| Tween ® 80 | 0.015% w/v |
| Sodium phosphate dibasic dihydrate | 0.142% w/v |
| 1M NaOH/HCl | pH adjusted to 7.4 ± 0.2 |
| Final volume | 1 mL |

In some embodiments, the MTX composition has the following formulation (F7):

| Component | Concentration |
| --- | --- |
| Methotrexate | 8 mg/mL |
| Sucrose | 7.5% w/v |
| Sodium phosphate dibasic dihydrate | 0.142% w/v |
| 1M NaOH/HCl | pH adjusted to 7.4 ± 0.2 |
| Final volume | 1 mL |

In some embodiments, the MTX composition has the following formulation (F8):

| Component | Concentration |
|---|---|
| Methotrexate | 8 mg/mL |
| Sucrose | 75 mg/mL |
| Sodium phosphate dibasic dihydrate | 0.113 mg/mL |
| 1M NaOH/HCl | As needed |
| Final volume | As needed to QS |

It is to be understood that variations in the above specific embodiments can be prepared according to the guidance provided herein.

5.2. Uses and Methods

In another aspect, the present disclosure provides use of the MTX compositions for preventing or reducing the risk of or treating PVR, intraocular lymphoma, or intraocular inflammation.

In some embodiments, the present disclosure provides use of the MTX compositions for preventing or reducing the risk of PVR or treating PVR. In some embodiments, a method of preventing or reducing the risk of or treating PVR comprises administering to a subject in need thereof a therapeutically effective amount of an MTX composition described herein. In some embodiments, the MTX composition is administered intravitreally.

In some embodiments, the present disclosure provides use of MTX in the preparation of a medicament for treating PVR, intraocular lymphoma, or intraocular inflammation, wherein the medicament comprises any of the compositions described above. In some embodiments, the medicament comprises MTX and a density enhancing agent, as described herein. In some embodiments, the medicament comprises MTX, a density enhancing agent, and a surfactant, as described herein.

In some embodiments, the subject for treatment with the MTX composition has a retinal injury, such as a tear or hole in the retina but which has not resulted in retinal detachment. In some embodiments, the subject for treatment with the MTX composition has undergone laser surgery (e.g., photocoagulation) for treatment for the retinal tear or hole. In some embodiments, the subject for treatment with the MTX composition has undergone cryopexy for treatment of the retinal tear or hole. In some embodiments, the subject for treatment with the MTX composition has undergone treatment for a retinal tear or hole and has one or more risk factors for PVR, as discussed further below. In some embodiments, the method comprises administering to an eye of a subject who has undergone laser surgery (e.g., laser retinopexy) or cryopexy for treatment of a retinal tear or hole a therapeutically effective amount of an MTX composition of the present disclosure.

In some embodiments, the subject for treatment with the MTX composition has suffered a retinal injury which is a retinal detachment. In some embodiments, the subject for treatment with the composition has suffered a primary retinal detachment. In some embodiments, the subject for treatment has a primary retinal detachment which is a rhegmatogenous retinal detachment. In some embodiments, subject for treatment with the MTX composition has suffered a secondary retinal detachment. In some embodiments, the subject for treatment with the MTX composition has suffered a rhegmatogenous retinal detachment, tractional retinal detachment, or a combined tractional-rhegmatogenous retinal detachment.

In some embodiments, the retinal detachment is a localized retinal detachment, and in some embodiments, the retinal detachment is a complete retinal detachment. In some embodiments, the method comprises administering to an eye of a subject afflicted with retinal detachment a therapeutically effective amount of a MTX composition of the present disclosure.

In some embodiments, the subject for treatment with the MTX composition has undergone treatment for a retinal detachment. In some embodiments, the method comprises administering to an eye of a subject treated for retinal detachment a therapeutically effective amount of a MTX composition of the present disclosure. In some embodiments, the subject for treatment with the MTX composition has undergone laser surgery (e.g., photocoagulation, laser retinopexy, etc.) for treatment of the retinal tear or hole associated with retinal detachment. In some embodiments, the subject for treatment with the MTX composition has undergone cryopexy for treatment of the retinal tear or hole associated with the retinal detachment. In some embodiments, the subject for treatment with the MTX composition has undergone pneumatic retinopexy to treat retinal detachment. In some embodiments, the subject for treatment with the MTX composition has undergone scleral buckling to treat retinal detachment. In some embodiments, the subject for treatment with the MTX composition has undergone a vitrectomy to treat retinal detachment, e.g., pars plana vitrectomy (PPV) with an intraocular tamponade, such as gas or silicone oil.

In some embodiments, the subject for treatment with the MTX composition is administered or has been administered intravitreally SiO in the affected eye, such as a tamponade for treating retinal detachment. In some embodiments, the SiO administered is SiO having a viscosity of at least 1000 centistoke. In some embodiments, the SiO administered has a viscosity of about 1000 to about 5000 centistoke. In some embodiments, the SiO administered is 1000 centistoke oil, in particular polydimethyl siloxane 1000 centistoke oil. In some embodiments, the SiO administered is 5000 centistoke oil, in particular polydimethyl siloxane 5000 centistoke oil.

In some embodiments, the subject for treatment with the MTX composition is administered or has been administered intravitreally heavy silicone oil (HSO), such as a tamponade for treating inferior retinal detachment. In some embodiments, the HSO is Oxane HD, Densiron 68, or HSV-45 3000. In some embodiments, the eye of the subject for treatment is administered or has been administered intravitreally perfluorocarbon liquids (PFCLs) or semifluorinated alkanes, such as perfluorohexyloctane (F6H8). PFCLs include perfluoro-n-octane (C8F18) and perfluorodecalin (C10F18).

In some embodiments, the MTX composition is administered by intravitreal injection into the SiO of a subject who has been treated with intravitreal SiO. In some embodiments, the MTX composition is co-administered with the SiO administered to the eye treated with the SiO and MTX composition. In some embodiments, the composition is present in the SiO when the SiO is administered into the posterior segment.

In some embodiments, the subject for treatment with the MTX composition has one or more risk factors for rhegmatogenous retinal detachment. In some embodiments, the subject for treatment with the MTX compositions has a prior history of one or more of the following: chronic ocular inflammation, infectious retinitis, multiple retinal detachments, large retinal breaks or giant retinal tears, multiple retinal breaks, ocular trauma, retinal detachment associated with vitreous hemorrhage, choroidal detachment, and combinations thereof.

In some embodiments, the subject for treatment with the MTX composition is characterized by vitreous or subretinal hemorrhage, excessive cryotherapy, pigment release during endodrainage, or combinations thereof.

In some embodiments, the compositions described herein can be used to treat other ocular diseases, disorders, or conditions that would benefit from treatment with methotrexate.

In some embodiments, the compositions herein are used to treat intraocular lymphoma. In some embodiments, a method of treating intraocular lymphoma comprises administering intravitreally to an eye of a subject with intraocular lymphoma a therapeutically effective amount of a composition disclosed herein, including the exemplary formulations disclosed herein.

In some embodiments, the intraocular lymphoma treated is primary vitreoretinal lymphoma (PVRL). Thus, the subject is afflicted or diagnosed with PVRL. In some embodiments, the intraocular lymphoma (e.g., PVRL) is accompanied by cerebral nervous system lymphoma (PCNSL). In some embodiments, the intraocular lymphoma is diffuse large B-cell lymphoma.

Administration and dosages for treatment of intraocular lymphoma are provided in more detail herein.

In addition to the disorders or PVR and intraocular lymphoma, the MTX compositions disclosed herein can also be used to treat inflammatory diseases, disorders, or conditions of the eye, particularly intraocular inflammation. In some embodiments, a method of treating intraocular inflammation comprises administering intravitreally to an eye of a subject with intraocular inflammation a therapeutically effective amount of a composition disclosed herein, including the exemplary formulations disclosed herein.

In some embodiments, the inflammatory diseases, disorders, or conditions for treatment with the MTX compositions herein include, among others, uveitis, for example pan uveitis, intermediate uveitis, and posterior uveitis, particularly non-infectious posterior uveitis; cystoid macular edema (CME); macular edema, for example accompanying uveitis or diabetic macular edema; choroidal neovascularization; and prosthetic membranopathy.

Administration and dosages for treatment of intraocular inflammation are provided in more detail herein.

5.3. Administration and Dosages

In some embodiments, the methods or use described herein include the use of a "therapeutically effective amount" of MTX composition described herein. A "therapeutically effective amount" refers to an amount sufficient to effect beneficial or desired results.

In some embodiments, the eye of the subject in need thereof is administered a therapeutically effective amount, which includes a prophylactically effective amount of the MTX composition of the present disclosure that prevents or reduces the risk of developing PVR. In some embodiments, the eye of the subject in need thereof is administered a therapeutically effective amount of the MTX composition of the present disclosure to treat PVR.

In some embodiments, the eye of the subject in need thereof is administered a therapeutically effective amount of the MTX composition of the present disclosure to treat intraocular lymphoma. In some embodiments, the eye of the subject in need thereof is administered a therapeutically effective amount of the MTX composition of the present disclosure to treat PVRL.

In some embodiments, the eye of the subject in need thereof is administered a therapeutically effective amount of the MTX composition of the present disclosure to prevent, reduce the risk of, or treat intraocular inflammation. In some embodiments, the eye of the subject in need thereof is administered a therapeutically effective amount of the MTX composition of the present disclosure to treat intraocular inflammation.

The amount of MTX administered can take into consideration, among others, the type of disease, disorder, or condition being treated (e.g., the nature or location of damage to the eye; the extent of intraocular lymphoma; or types of intraocular inflammation), the age and sex of the subject, the presence of risk factors, and the type of treatment given to the subject to treat the eye.

A therapeutically effective amount can be administered in one or more administrations, applications, or dosages. In some embodiments, the eye of the subject is administered the MTX composition described herein sufficient to deliver MTX at a dose of about 25 µg to about 600 µg. In some embodiments, the eye of the subject is administered a dose of MTX of about 30 µg to about 580 µg, about 35 µg to about 560 µg, about 40 µg to about 540 µg, about 45 µg to about 520 µg, about 50 µg to about 500 µg, about 60 µg to about 480 µg, about 70 µg to about 460 µg, about 80 µg to about 440 µg, about 90 µg to about 430 µg, about 100 µg to about 420 µg, about 120 µg to about 400 µg, about 140 µg to about 380 µg, about 160 µg to about 360 µg, about 180 µg to about 340 µg, or about 200 µg to about 320 µg, In some embodiments, the dose of MTX is about 200 µg to about 600 µg, or about 300 µg to about 500 µg.

In some embodiments, the eye of the subject is administered a dose of MTX of about 25 µg, about 30 µg, about 35 µg, about 40 µg, about 45 µg, about 50 µg, about 60 µg, about 65 µg, about 70 µg, about 75 µg, about 80 µg, about 85 µg, about 90 µg about 95 µg, about 100 µg, about 110 µg, about 120 µg, about 130 µg, about 140 µg, about 150 µg, about 160 µg, about 170 µg, about 180 µg, about 190 µg, about 200 µg, about 210 µg, about 220 µg, 230 µg, 240 µg, 250 µg, 260 µg, 270 µg, 280 µg, 290 µg, about 300 µg, about 320 µg, about 340 µg, about 360 µg, about 300 µg, about 350 µg, about 400 µg, about 450 µg, about 500 µg, about 550 µg, or about 600 µg. Preferably, the dose of MTX is about 200 µg, 300 µg, 400 µg, or about 500 µg.

In some embodiments for intravitreal administration, the volume of composition administered is suitable for intravitreal administration. By way of example and not limitation, the volume can be adjusted if the administration is intravitreally into gas or SiO filled eye. In some embodiments, the volume of composition administered is about 20 µl to about 300 µl, about 25 µl to about 200 µl, about 30 µl to about 190 µl, about 35 µl to about 180 µl, about 40 µl to about 170 µl, about 45 µl to about 150 µl, about 50 µl to about 140 µl, about 55 µl to about 130 µl, about 60 µl to about 120 µl, about 70 µl to about 110 µl, or about 80 µl to about 100 µl.

In some embodiments for intravitreal administration, the volume of composition administered is about 25 µl, about 30 µl, about 35 µl, about 40 µl, about 45 µl, about 50 µl, about 60 µl, about 70 µl, about 80 µl, about 90 µl, about 100 µl, about 120 µl, about 140 µl, about 160 µl, about 180 µl, about 200 µl, about 220 µl, about 240 µl, about 260 µl, about 280 µl, or about 300 µl. An exemplary volume for intravitreal administration is 100 µl.

In some embodiments, the MTX composition is administered at a frequency and duration to provide a prophylactic effect or to treat a disease, disorder, or condition disclosed herein in the affected eye.

In some embodiments, the MTX composition is administered at a frequency and duration to provide a prophylactic effect or to treat PVR.

In some embodiments for treating PVR, the dose, frequency, and duration can be adjusted taking into consideration factors such as, among others, extent of retinal injury, location of the retinal injury, type of surgery used to treat the eye damage, the age and sex of the subject, duration of tamponade needed with gas or SiO, and presence of one or more risk factors for PVR. In some embodiments, the MTX composition is administered once a day, once every two days, once every three days, once every four days, once every five days, once every 6 days, or once every seven days. In some embodiments, the MTX composition is administered once every week, or once every 2 weeks, once every three weeks, or once a month.

In some embodiments, the following is used to treat PVR. In some embodiments, the MTX composition is administered more than once per day, for example two times per day or three times per day. In some embodiments, the subject is administered the MTX composition twice or three times per day postoperatively, for example, in the day surgery has been completed, and/or 1 day, 2 days, 3 days or 4 days following surgical treatment.

In some embodiments, the MTX composition can be administered at least once a day for 3, 4, 5, 6, or 7 days following initial retinal damage and/or post-operative surgery followed by a lower frequency of administration. In some embodiments, the MTX composition is administered at least once a day for at least for two weeks followed by a lower frequency of administration.

In some embodiments, the duration of treatment is for at least 2 days, at least 3 days, at least 4 days, at least 5 days, at least 6 days, at least one week, at least two weeks, at least 3 weeks, at least 1 month, at least 2 months, at least 3 months, at least 4 months, at least 5 months, at least 6 months, at least 7 months, at least 8 months, at least 9 months, at least 10 months, or at least 12 months (i.e., one year). In some embodiments, where the treatment involves gas or SiO, e.g., as a tamponade, the treatment duration is until completion of treatment with the gas or removal of the SiO, respectively. In some embodiments, the treatment with the MTX composition is continued following completion of treatment with the gas or removal of the SiO, for example where the subject has one or more risk factors for PVR.

In some embodiments, intravitreal administration of the MTX composition for treating a disease, disorder, or condition described herein is performed according to standard methods used in the art. In some embodiments, intravitreal administration is performed aseptically after the topical application of anesthesia and an antiseptic agent, e.g., 5% povidone iodine, to the conjunctival sac. In some embodiments, eye of the subject is administered an intravitreal injection of the MTX composition, for example with a 30-gauge needle.

In some embodiments for treating PVR, where the MTX composition is administered intravitreally into SiO in the eye, the subject is maintained in an appropriate position (e.g., lying face up) following administration of SiO, for the MTX composition to transit through the SiO, and in some embodiments, sufficient time for transit through the SiO and dispersion of the MTX composition in the aqueous phase for adsorption into the retinal tissues, especially over the posterior pole. In some embodiments, the patient may be positioned in other positions (e.g., lying on one's side) to direct the methotrexate to a specific area. In some embodiments, the subject is positioned appropriately for at least 30 min, at least 25 min, at least 20 min, at least 15 min, at least 10 min, or at least 5 min following administration of the MTX composition into the SiO.

In some embodiments, the MTX composition is administered at a frequency and duration to effective to treat intraocular lymphoma, e.g., PVRL.

In some embodiments for treating intraocular lymphoma, the dose, frequency, and duration can be adjusted taking into consideration factors such as, among others, the severity or stage of the intraocular lymphoma and other conditions, such as the presence or absence of accompanying PCNSL. In some embodiments, the MTX composition is administered once every 4 weeks (month), once every two weeks, once a week, two times a week, three times a week, or four times a week to treat intraocular lymphoma.

In some embodiments for treating intraocular lymphoma, the treatment regimen includes an induction phase, and optionally a consolidation phase, and/or a maintenance phase.

In some embodiments, the induction phase is administration of the MTX composition two times a week, up to four times a week.

In some embodiments, the consolidation phase, when present, comprises administration once a week or two times a week.

In some embodiments, the maintenance phase, when present, comprises administration once every two weeks or once every month.

In some embodiments for treating intraocular lymphoma, the dose administered is sufficient to provide a therapeutic effect. In some embodiments, any of the doses disclosed above can be used in an effective amount for treating intraocular lymphoma. In some embodiments, the dose of MTX administered is about 100 to 800 μg, about 200 to 600 μg, or about 300 to 500 μg.

In some embodiments, the dose of MTX administered for treating intraocular lymphoma is about 100 μg, about 200 μg, about 300 μg, about 400 μg, about 500 μg, about 600 μg, about 700 μg, or about 800 μg. In preferred embodiments, the dose of MTX administered is about 200 μg, about 300 μg, about 400 μg, or about 500 μg. In some embodiments, the dose of MTX administered is about 400 μg.

In some embodiments for treating intraocular lymphoma, the dose administered is sufficient to provide a therapeutic effect. In some embodiments, the dose of MTX administered is about 100 to 800 μg/0.1 mL, about 200 to 600 μg/0.1 mL, or about 300 to 500 μg/0.1 mL.

In some embodiments, the dose of MTX administered for treating intraocular lymphoma is about 100 μg/0.1 mL, about 200 μg/0.1 mL, about 300 μg/0.1 mL, about 400 μg/0.1 mL, about 500 μg/0.1 mL, about 600 μg/0.1 mL, about 700 μg/0.1 mL, or about 800 μg/0.1 mL. In preferred embodiments, the dose of MTX administered is about 200 μg/0.1 mL, about 300 μg/0.1 mL, about 400 μg/0.1 mL, or about 500 μg/0.1 mL. In some embodiments, the dose of MTX administered is about 400 μg/0.1 mL.

In some embodiments for treating intraocular lymphoma, the treatment with MTX is in combination with a secondary therapeutic agent effective for treatment of the lymphoma. In some embodiments, the secondary therapeutic administered in combination with the MTX is an anti-CD20 antibody. In some embodiments, the anti-CD20 antibody is selected from rituximab, ocrelizumab, veltuzumab, obinutuzumab, and ofatumumab.

In some embodiments, the MTX composition is administered at a frequency and duration to effective to treat intraocular inflammation. In some embodiments, the intraocular inflammation for treatment is uveitis, for example pan uveitis, intermediate uveitis, or posterior uveitis, particularly non-infectious posterior uveitis; cystoid macular edema (CME); macular edema, for example accompanying uveitis, or diabetic macular edema; choroidal neovascularization; and prosthetic membranopathy.

In some embodiments for treating intraocular inflammation, the dose, frequency, and duration can be adjusted taking into consideration factors such as, among others, the type of intraocular inflammation, and the severity or stage of the intraocular inflammation. In some embodiments, the MTX composition is administered once every 4 weeks (month), once every two weeks, once a week, two times a week, three times a week, or four times a week to treat intraocular inflammation.

In some embodiments for treating intraocular inflammation, the treatment regimen includes an induction phase, and optionally a consolidation phase, and/or a maintenance phase.

In some embodiments, the induction phase is administration of the MTX composition two times a week, up to four times a week.

In some embodiments, the consolidation phase, when present, comprises administration once a week or two times a week.

In some embodiments, the maintenance phase, when present, comprises administration once every two weeks or once every month.

In some embodiments for treating intraocular inflammation, the dose administered is sufficient to provide a therapeutic effect. In some embodiments, any of the doses disclosed above can be used in an effective amount for treating intraocular inflammation. In some embodiments, the dose of MTX administered is about 100 to 800 μg, about 200 to 600 μg, or about 300 to 500 μg.

In some embodiments, the dose of MTX administered for treating intraocular inflammation is about 100 μg, about 200 μg, about 300 μg, about 400 μg, about 500 μg, about 600 μg, about 700 μg, or about 800 μg. In preferred embodiments, the dose of MTX administered is about 200 μg, about 300 μg, about 400 μg, or about 500 μg. In some embodiments, the dose of MTX administered is 400 μg.

In some embodiments for treating intraocular inflammation, the dose administered is sufficient to provide a therapeutic effect. In some embodiments, the dose of MTX administered is about 100 to 800 μg/0.1 mL, about 200 to 600 μg/0.1 mL, or about 300 to 500 μg/0.1 mL.

In some embodiments, the dose of MTX administered for treating intraocular inflammation is about 100 μg/0.1 mL, about 200 μg/0.1 mL, about 300 μg/0.1 mL, about 400 μg/0.1 mL, about 500 μg/0.1 mL, about 600 μg/0.1 mL, about 700 μg/0.1 mL, or about 800 μg/0.1 mL. In preferred embodiments, the dose of MTX administered is about 200 μg/0.1 mL, about 300 μg/0.1 mL, about 400 μg/0.1 mL, or about 500 μg/0.1 mL. In some embodiments, the dose of MTX administered is about 400 μg/0.1 mL.

5.4. Kits

In another aspect, the MTX composition is provided in the form of a kit. In some embodiments, the MTX composition in the kit is provided in a multi-dose vial. In some embodiments, the MTX composition in the kit is provided as single use vials. In some embodiments, the kit comprises one or more single use vials of the MTX composition. In some embodiments, the MTX composition is provided in the form of a dry composition for reconstitution with an appropriate solvent, such as pyrogen free sterile water or buffer. In some embodiments, the kit when provided as a dry composition includes a vial of solvent for reconstitution of MTX solution for injection.

In some embodiments, the kit further comprises a syringe for injection of the MTX composition. In some embodiments, the kit includes one or more syringes for injection of the MTX composition. In some embodiments, the MTX composition is provided in pre-filled syringes for administration into an eye of a subject.

In certain embodiments, the kit also includes prescribing information for proper use of the compositions. The information may be in the form of printed material or on a computer readable medium.

The following examples are provided to further illustrate the embodiments of the present disclosure. The examples described are illustrative only and are not intended to limit the scope of the invention in any way.

6. EXAMPLES

Example 1: Preparation of Compositions and Assessment of Transit Through Silicone Oil Water is placed in a suitable container, and each ingredient, e.g., surfactants, buffer, density building agent, methotrexate, etc., as appropriate for the formulation is added and dissolved in the solution one at a time. The pH is adjusted to 7.4±0.2 by addition of 1M sodium hydroxide or HCl. Water is added to make up to the desired final volume.

The impact of formulation composition on the travel time of the methotrexate through silicone layers of varying viscosity and amount was investigated using two grades of silicone oil: Polydimethyl siloxane 1,000 cps (Sigma Aldrich, UK) and 5,000 cps (Mistral industrial chemicals, UK).

1. Two heights of silicone oil were tested: 0.5 cm or 1 cm of oil was placed on top of 2 mL PBS buffer to confirm best height to use.
2. A drop of formulation (~50 mg) was placed at the top of silicone layer.

The time taken for the API (formulation drop, yellow in color) to travel was monitored (cm/min), as well as visual observations for the distribution of the formulation phase into aqueous phase after traveling through the silicone phase, e.g., spontaneous, slow, etc.

The transit times of several different formulations examined are provided in FIG. 1.

Several of the formulations were also assessed for the number of times the formulation passes through the oil interface within a 2 h time period. Each formulation was measured for a maximum of 2 h and the results represent the number of times the formulation passed across the silicone oil-PBS buffer interface in the assessed time period. The total number of times at both heights and both viscosities (out of 9 tests) and the % is provided in the table below.

TABLE 1

| Formulation | Silicone Oil | | | | No. of times crossed interface (%) |
|---|---|---|---|---|---|
| | 1000 centistoke | | 5000 centistoke | | |
| | 0.5 mL | 1 mL | 0.5 mL | 1 mL | |
| F1 | 1 | 0 | 1 | 1 | 3 out of 12 (25%) |
| F4 | 1 | 2 | 2 | 2 | 7 out of 12 (58%) |
| F5 | 1 | 2 | 3 | 3 | 9 out of 12 (75%) |
| F6 | 2 | 2 | 3 | 2 | 9 out of 12 (75%) |

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. A composition suitable for intravitreal administration, comprising:
methotrexate at a concentration of about 7 mg/mL to about 9 mg/mL, and a density enhancing agent selected from sucrose, trehalose, glucose, polyvinyl acetate, polyvinyl alcohol (PVA), polyvinylpyrrolidone (PVP), carboxymethylcellulose, hydroxypropyl methylcellulose, hydroxypropyl cellulose, hydroxyethyl cellulose, polyethylene glycol (PEG), glycerol, poly(lactide) (PLA), poly(lactide-co-glycolide) (PLGA), polyglycolide (PGA), polyhydroxybutyric acid, polycaprolactone, polyvalerolactone, polyphosphazene, polyorthoester, cyclodextrin, or mixtures thereof,
wherein the composition has a density of about 1.0 to about 1.20 g/cm$^3$ at 20° C.

2. The composition of claim 1, wherein the composition has a transit rate of less than 10 min in 1 mL of silicone oil (SiO) having a viscosity of at least 1000 centistoke and depth of 1 cm.

3. The composition of claim 2, wherein the SiO is polydimethyl siloxane 5000 centistoke oil or polydimethyl siloxane 1000 centistoke oil.

4. The composition of claim 1, wherein the composition has a density of at least about 1.03 g/cm$^3$ at 20° C.

5. The composition of claim 1, wherein the density enhancing agent is PEG.

6. The composition of claim 5, wherein the PEG is PEG 4000.

7. The composition of claim 6, wherein the PEG 4000 is at a concentration of about 5% to 10% w/v of the composition.

8. The composition of claim 7, wherein the PEG 4000 is at about 7.5% w/v of the composition.

9. The composition of claim 1, further comprising a surfactant.

10. The composition of claim 9, wherein the surfactant comprises a non-ionic surfactant.

11. The composition of claim 9, wherein the surfactant is selected from polyoxyethylene (20) sorbitan monolaurate, polyoxyethylene (20) sorbitan monopalmitate, polyoxyethylene (20) sorbitan monostearate, polyoxyethylene (20) sorbitan mono-oleate, polyoxyethylene (20) sorbitan tristearate, polyoxyethylene (20) sorbitan tri-oleate, sorbitan monopalmitate, sorbitan monostearate, sorbitan mono-oleate, sorbitan tristearate, and sorbitan trioleate.

12. The composition of claim 11, wherein the surfactant is polyoxyethylene (20) sorbitan monolaurate or polyoxyethylene (20) sorbitan mono-oleate.

13. The composition of claim 10, wherein the surfactant is present at a concentration of 0.0015% w/v to about 0.05% w/v.

14. The composition of claim 1, further comprising a buffering agent.

15. The composition of claim 14, wherein the buffering agent is selected from borate, phosphate, bicarbonate, carbonate, citrate, tetraborate, biphosphate, tromethamine, hydroxyethyl morpholine, and THAM (trishydroxymethyl-amino-methane).

16. The composition of claim 1, wherein the composition is at a pH of about 5.5 to about 8.5.

17. The composition of claim 16, wherein the pH is about 6.5 to about 7.5.

18. The composition of claim 1, wherein the density enhancing agent is sucrose present at a concentration of about 7.5% w/v of the composition.

* * * * *